United States Patent [19]

Cooper et al.

[11] Patent Number: 5,736,589
[45] Date of Patent: Apr. 7, 1998

[54] ABSORBABLE POLYALKYLENE DIGLYCOLATES

[75] Inventors: Kevin Cooper, Warren; Angelo Scopelianos, Whitehouse Station, both of N.J.

[73] Assignee: Ethicon, Inc., Somerville, N.J.

[21] Appl. No.: 690,374

[22] Filed: Jul. 30, 1996

Related U.S. Application Data

[60] Continuation of Ser. No. 505,498, Jul. 21, 1995, abandoned, which is a division of Ser. No. 375,020, Jan. 19, 1995, abandoned.

[51] Int. Cl.$^6$ .......................... C08G 63/91; C08G 63/21; C08G 63/12
[52] U.S. Cl. .................. 522/43; 522/44; 522/48; 522/63; 522/68; 522/104; 522/108; 525/34; 525/42; 528/301; 528/303
[58] Field of Search ............. 525/34, 42; 528/301, 528/303; 522/44, 68, 43, 63, 48, 104, 108

[56] References Cited

U.S. PATENT DOCUMENTS

| | | | |
|---|---|---|---|
| 3,280,077 | 10/1966 | Case . | |
| 3,567,494 | 3/1971 | Fitko | 528/303 |
| 4,206,025 | 6/1980 | Urancken | 528/303 |
| 4,502,976 | 3/1985 | Heller | 528/300 |
| 4,506,672 | 3/1985 | Bichon | 128/335.5 |

*Primary Examiner*—David Buttner
*Attorney, Agent, or Firm*—Emil Richard Skula

[57] ABSTRACT

Absorbable polymers and blends of acrylated poly(alkylene diglycolate)s and aliphatic polyesters based on lactone monomers such as lactide, glycolide, e-caprolactone, p-dioxanone, and trimethylene carbonate are described. The polymers and blends exhibit a broad range of properties, useful in a variety of medical devices.

2 Claims, 6 Drawing Sheets

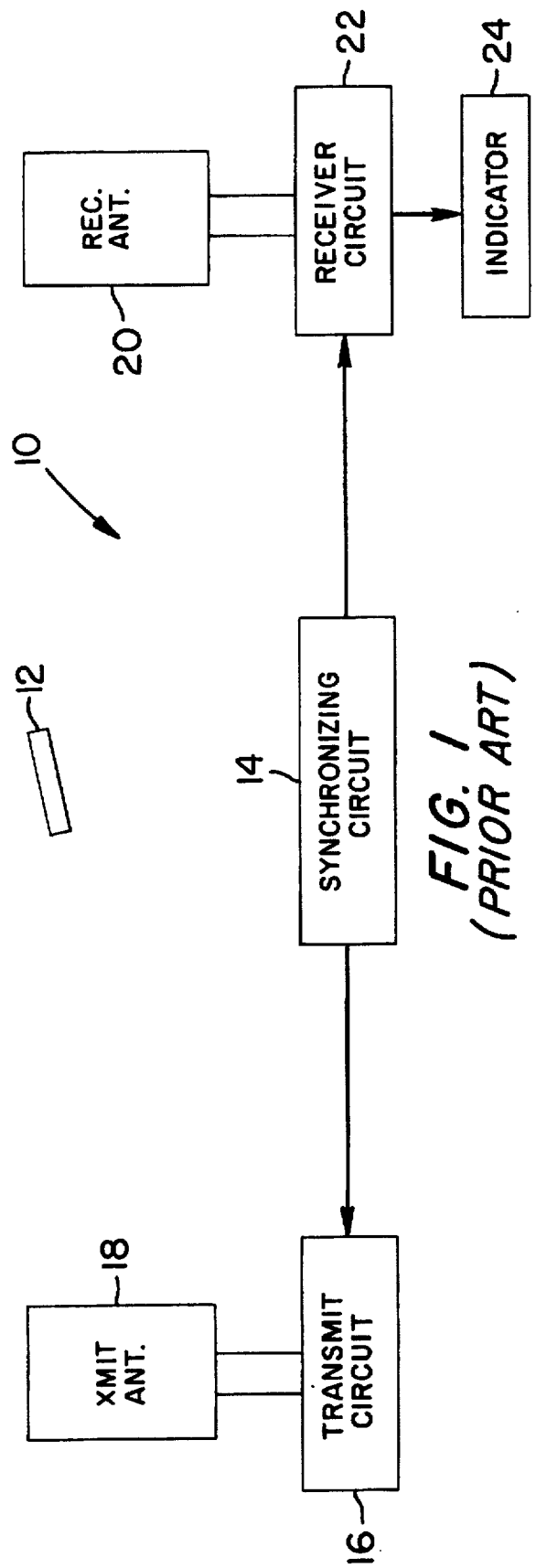
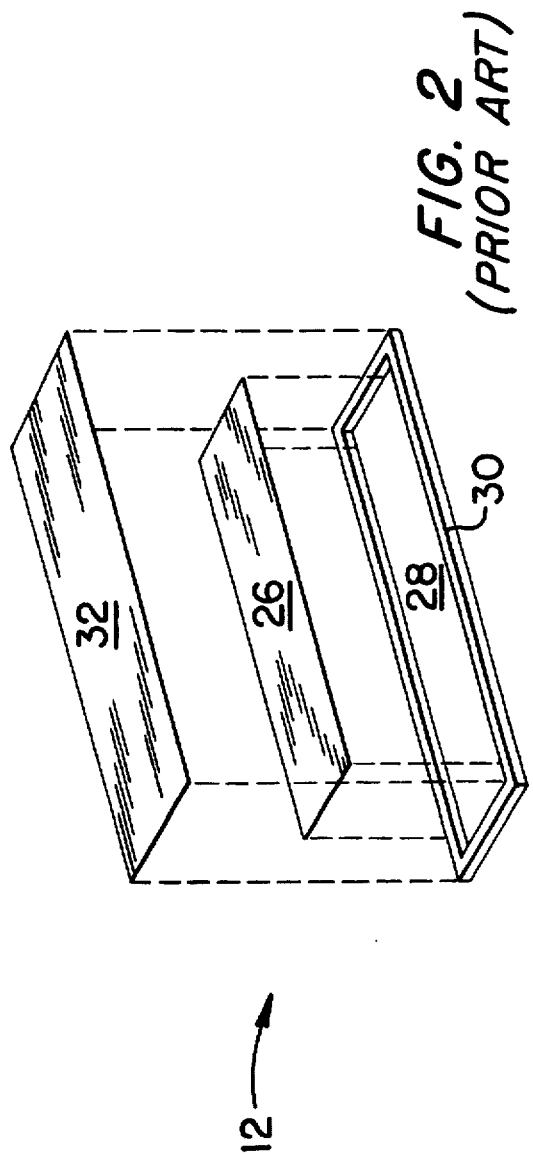
FIG. 1 (PRIOR ART)
FIG. 2 (PRIOR ART)

ABSORBABLE POLYALKYLENE DIGLYCOLATES

This is a continuation of application Ser. No. 08/505,498, filed Jul. 21, 1996, now abandoned, which is a division of application Ser. No. 08/375,020, filed Jan. 19, 1995, which is now abandoned and hereby incorporated by reference.

TECHNICAL FIELD

The field of art to which this invention relates is polymers, more specifically, biocompatible, absorbable homopolymer and copolymers as well as blends. Especially, homo- and co-polymers and blends of poly(alkylene diglycolate)s and aliphatic polyesters of lactide, glycolide, e-caprolactone, p-dioxanone, and trimethylene carbonate.

BACKGROUND OF THE INVENTION

Polymers, including homopolymers and copolymers, which are both biocompatible and absorbable in vivo are well known in the art. Such polymers are typically used to manufacture medical devices which are implanted in body tissue and absorb over time. Examples of such medical devices manufactured from these absorbable biocompatible polymers include suture anchor devices, sutures, staples, surgical tacks, clips, plates and screws, drug delivery devices, adhesion prevention films and foams, and tissue adhesives, etc.

Absorbable, biocompatible polymers useful for manufacturing medical devices include both natural and synthetic polymers. Natural polymers include cat gut, cellulose derivatives, collagen, etc. Synthetic polymers may consist of various aliphatic polyesters, polyanhydrides, poly(orthoester)s, and the like. Natural polymers typically absorb by an enzymatic degradation process in the body, while synthetic absorbable polymers typically degrade by a hydrolytic mechanism.

Synthetic absorbable polymers which are typically used to manufacture medical devices include homopolymers such as poly(glycolide), poly(lactide), poly(e-caprolactone), poly(trimethylene carbonate) and poly(p-dioxanone) and copolymers such as poly(lactide-co-glycolide), poly(e-caprolactone-co-glycolide), and poly(glycolide-co-trimethylene carbonate). The polymers may be statistically random copolymers, segmented copolymers, block copolymers, or graft copolymers. It is also known that both homopolymers and copolymers can be used to prepare blends.

U.S. Pat. Nos. 3,997,512, 4,048,256, 4,076,798, 4,095,600, 4,118,470, and 4,122,129, describe several biocompatible, absorbable, low Tg, aliphatic polyesters known as poly(alkylene diglycolate)s. These polymers are prepared from the polycondensation of diglycolic acid and glycols such as ethylene glycol, diethylene glycol, 1,2-propylene glycol, 1,3-propylene glycol, and the like. These film forming, non-branched, non-crosslinked, linear polymers have found use in drug delivery.

However, there is a constant need in this art for new polymer compositions having improved properties when formed into medical devices. For example, there is a great need for soft, flexible, elastomeric, low melting or liquid polymers for use as tissue adhesives and sealants, bone waxes, cartilage replacements, adhesion prevention barriers, and soft tissue augmentation fillers.

Consequently, for applications such as bone waxes or cartilage replacement, it would be highly desirable to have a polymeric material having characteristics such as pliability, and elasticity as found in highly branched or crosslinked gels.

Furthermore, materials used for biomedical applications such as defect fillers, and tissue adhesives and sealants require characteristics such as hydrophilicity, ease of application (i.e., low viscosity liquid) and quick setting times (i.e., water or light curing).

Accordingly, what is needed in this art are novel polymeric materials which are liquid or low melting, soft, flexible, and elastomeric.

Surprisingly, we have discovered that by selecting appropriate combinations of poly(alkylene diglycolate) homo- or co-polymers, or by post-polymerizing/crosslinking pendant acrylate groups on poly(alkylene diglycolate)s, or by preparing copolymers or blends of poly(alkylene diglycolate)s with aliphatic polyesters such as poly(e-caprolactone), poly(p-dioxanone), and poly(trimethylene carbonate), materials with a wide range of unique physical characteristics, such as those described above, useful as tissue adhesives and sealants, bone wax, cartilage replacement, adhesion prevention barriers, and soft tissue augmentation fillers can be prepared.

DISCLOSURE OF THE INVENTION

Accordingly, novel, absorbable, biocompatible, poly(alkylene diglycolate) homo- and co-polymers and copolymers or blends with aliphatic polyesters are disclosed. Additionally, poly(alkylene diglycolate)s or poly(alkylene diglycolate) copolymers with pendant acrylate groups are disclosed.

More specifically, the poly(alkylene diglycolate) homopolymer and copolymers of the present invention are prepared by a condensation polymerization using a dicarboxylic acid and alcohol monomers. That is, the dicarboxylic acid or ester of diglycolic acid in conjunction with di-, tri-, and tetra-functional alcohols as well as hydroxyl terminated poly(ethylene glycol)s (i.e., PEG's).

Additionally, for copolymers which comprise diols such as ethylene glycol, 1,3-propanediol, and the like, as well as tri- and tetra-functional alcohols, and hydroxyl terminated PEG's, the use of diols will be limited so as to lead to polymers where about 95 mole percent, more preferably 90 mole percent, of the repeating units contain multifunctional alcohols or hydroxyl terminated PEG's.

Another aspect of the present invention are poly(alkylene diglycolate)-co-(aliphatic polyester) polymers which will typically consist of about 5 mole percent to about 95 mole percent of the poly(alkylene diglycolate) repeating units, more preferably about 10 mole percent to about 90 mole percent of poly(alkylene diglycolate) repeating units.

Yet another aspect of the present invention are blends of poly(alkylene diglycolate) and aliphatic polyesters which will typically consist of about 5 weight percent to about 95 weight percent of the poly(alkylene diglycolate)s, more preferably about 10 weight percent to about 90 weight percent poly(alkylene diglycolate)s.

Still yet another aspect of the present invention are poly(alkylene diglycolate)s of the above described polymers, copolymers and blends which are post-polymerized to form pendant acrylate groups.

Yet another aspect of the present invention is a biomedical device, especially implantable devices such as tissue adhesives and sealants, bone wax, cartilage replacement, adhesion prevention barriers, and soft tissue augmentation fillers made from the above-described polymers and blends.

The foregoing and other features and advantages of the invention will become more apparent from the following description and examples and accompanying drawings.

BRIEF DESCRIPTION OF THE DRAWINGS

FIG. 1 illustrates a synthetic process for the preparation of poly(alkylene diglycolate) branched and crosslinked polymers.

FIG. 2 illustrates a synthetic process for the preparation of poly(alkylene diglycolate) polymers with pendant acrylate groups.

DESCRIPTION OF THE PREFERRED EMBODIMENTS

Figure 3A:
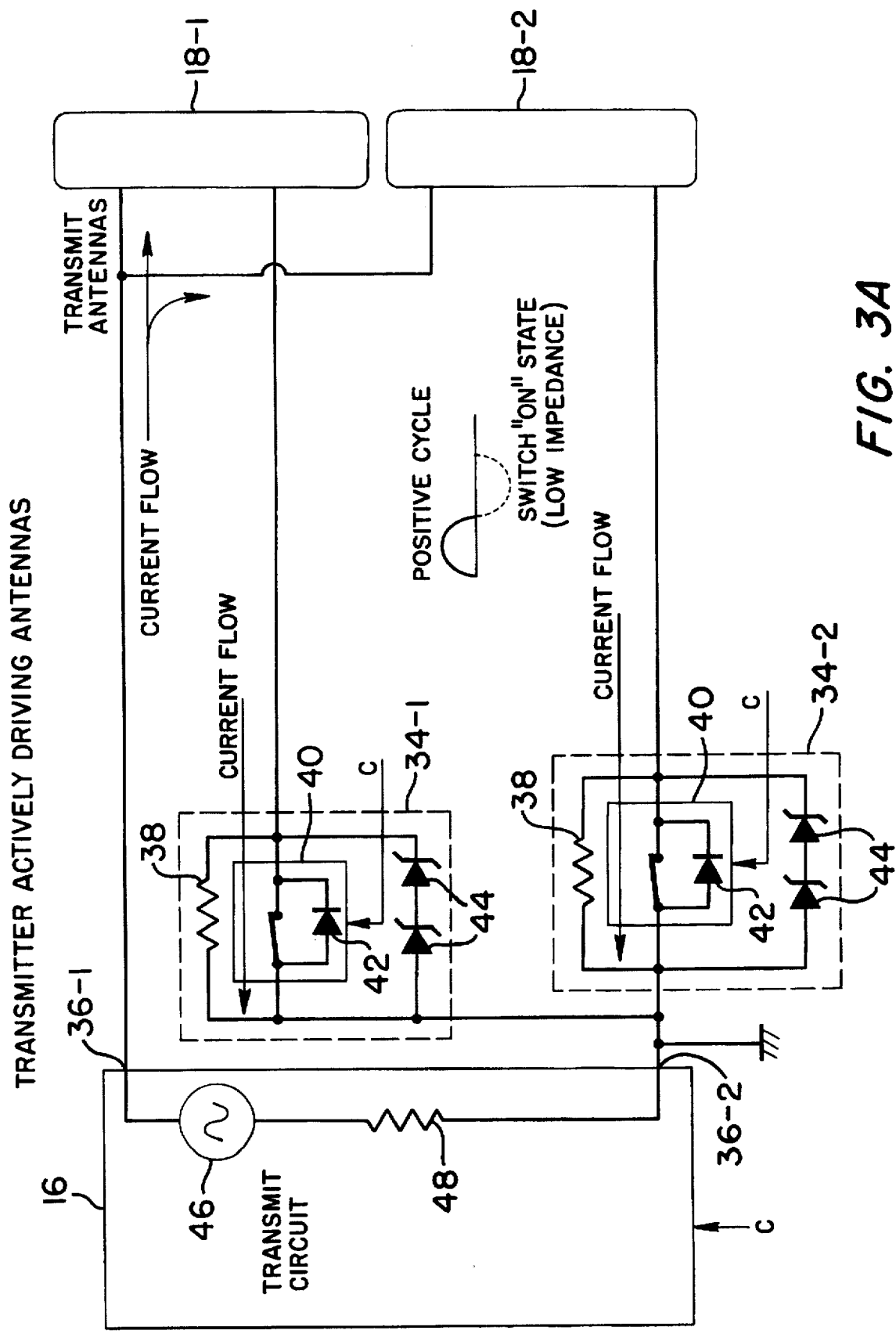
FIG. 3 illustrates a synthetic process for the preparation of copolymers of poly(alkylene diglycolate)s and aliphatic polyesters.

The aliphatic poly(alkylene diglycolate)s useful in the practice of the present invention will typically be synthesized by conventional techniques using conventional processes. For example, in a condensation polymerization, a dicarboxylic acid (diglycolic acid) and an alcohol (i.e., glycerol) is polymerized in the presence of a catalyst at elevated temperatures and reduced pressures. The catalyst is preferably tin based, although any conventional catalyst may be used, e.g., stannous octoate, and is present in the monomer mixture at a sufficiently effective molar ratio of monomer to catalyst, e.g., ranging from about 10,000/1 to about 100,000/1, or other conventional molar ratios. The reaction is typically carried out at a temperature range from about 80° C. to about 220° C., preferably from about 160° C. to about 200° C., under an inert atmosphere until esterification of diglycolic acid is complete, followed by polymerization under reduced pressure until the desired molecular weight and viscosity are achieved.

Suitable alcohols for the preparation of poly(alkylene diglycolate) polymers include, but are not limited to, glycerol, pentaerythitol, trimethylolpropane, slightly to substantially water soluble hydroxyl terminated poly(ethylene glycol)s of weight average molecular weight of about 100 grams per mole to about 40,000 grams per mole, ethylene glycol, 1,2-propanediol, 1,3-propanediol, 1,4-butylene glycol, dipropylene glycol, 1,5-pentanediol, 1,6-hexanediol, 1,7-heptanediol, 1,8-octanediol, and the like. It should be noted that the term substantially water soluble as used herein is defined as meaning that the solubility of the poly(ethylene glycol) in an aqueous solution is greater than 1 gram per 100 mL of water, whereas the term slightly water soluble is defined as meaning that the solubility of the poly(ethylene glycol) in an aqueous solution is less than 1 gram per 100 mL of water.

The aliphatic polyesters useful in the practice of the present invention will typically be synthesized by conventional techniques using conventional processes. For example, in a ring opening polymerization, the aliphatic lactone monomers are polymerized in the presence of a conventional organometallic catalyst and an initiator at elevated temperatures. The organometallic catalyst is preferably tin based, e.g., stannous octoate, and is present in a sufficiently effective amount in the monomer mixture, preferably at a molar ratio of monomer to catalyst ranging from about 10,000/1 to about 100,000/1. The initiator is typically an alkanol, a glycol, a hydroxyacid, or an amine, or any conventional initiator and is present in the monomer mixture in a sufficiently effective amount, preferably at a molar ratio of monomer to initiator ranging from about 100/1 to about 5000/1. The polymerization is typically carried out at a temperature range from about 80° C. to about 220° C., preferably from about 160° C. to about 200° C., until the desired molecular weight and viscosity are achieved.

Suitable lactone monomers include, but are not limited to, glycolide, lactide (l, d, dl, meso), p-dioxanone, trimethylene carbonate, e-caprolactone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicyclooctane-7-one and combinations of two or more thereof. Preferred lactone monomers include glycolide, lactide, p-dioxanone, trimethylene carbonate and e-caprolactone.

The copolymers of poly(alkylene diglycolate)s and aliphatic polyesters useful in the practice of the present invention will typically be synthesized by conventional techniques using conventional processes. For example, a preformed poly(alkylene diglycolate) of weight average molecular weight of about 100 to about 100,000 grams per mole and a preformed aliphatic polyester of weight average molecular weight of about 100 to about 100,000 grams per mole are transesterified in the presence of a conventional organometallic catalyst at elevated temperatures. The organometallic catalyst is preferably tin based, e.g., stannous octoate, and is present in a sufficiently effective amount in the mixture at a molar ratio of polymer to catalyst ranging from about 10,000/1 to about 100,000/1. The transesterification is typically carried out at a temperature range from about 80° C. to about 220° C., preferably from about 160° C. to about 200° C. until the desired molecular weight and viscosity are achieved.

Under the above described conditions, the homopolymers and copolymers of poly(alkylene diglycolate)s and aliphatic polyesters, will typically have a weight average molecular weight of about 2,000 grams per mole to about 200,000 grams per mole, more typically about 5,000 grams per mole to about 100,000 grams per mole, and preferably about 10,000 grams per mole to about 70,000 grams per mole. These molecular weights are sufficient to provide an effective inherent viscosity, typically between about 0.05 to about 3.0 deciliters per gram (dL/g), more typically 0.1 to about 2.5 dL/g, and most preferably 0.2 to about 2.0 dL/g as measured in a 0.1 g/dL solution of hexafluoroisopropanol (HFIP) at 25° C.

The poly(alkylene diglycolate) homo- and co-polymers will typically consist of about 5 mole percent to about 95 mole percent, and more preferably about 10 mole percent to about 90 mole percent of repeating units with tri- and/or tetra-functional alcohols and/or hydroxyl terminated poly(ethylene glycol)s, with the remaining portions consisting of repeating units with diols. The lower limit of multi-functional alcohols and poly(ethylene glycol)s in the homo- and co-polymers is desirable because the addition of 5 mole percent leads to polymers which have fewer branches or crosslinks and provides for materials which are useful in applications such as injectable defect fillers and tissue adhesives and sealants due to their low viscosities. The upper limit of multi-functional alcohols and poly(ethylene glycol)s in the homo- and co-polymers is desirable because the addition of 95 mole percent leads to polymers which are highly branched or crosslinked and provides for materials which are useful in applications such as, preformed defect fillers, bone waxes, and cartilage replacements due to their elastic properties. In addition, the incorporation of hydroxyl terminated poly(ethylene glycol)s in the poly(alkylene diglycolate)s is desirable because it leads to polymers which are useful, for example, as coatings for use as adhesion prevention barriers due to their hydrophilic, partially water soluble, gel-like properties.

The copolymers of poly(alkylene diglycolate)s and aliphatic polyesters will typically consist of about 5 mole percent to about 95 mole percent, more preferably 10 mole percent to 90 mole percent of poly(alkylene diglycolate)s. The lower and upper limits of poly(alkylene diglycolate) provides for copolymers with a desirable range of strength, stiffness and absorption profiles.

Additionally, the above described polymers, copolymers and blends can be post-polymerized to form pendant acrylate groups by a method consisting of reacting hydroxyl pendant side groups on poly(alkylene diglycolate) homo- and co-polymers with acryloyl chloride, or other unsaturated acid halide containing compounds such as methacryloyl chloride, trans-crontonyl chloride, dimethyl acryloyl chloride, and other acrylates, diacrylates, oligoacrylates, methacrylates, dimethacrylates, oligomethacrylates, and the like, via esterification at temperatures of 25° C. to 75° C. for 1 to 12 hours under an inert atmosphere. Additionally, other biologically acceptable photopolymerizable groups can be used.

Furthermore, once formed, these acrylate groups can be polymerized quickly, forming water or partially water soluble crosslinked gels, within a few seconds to a few minutes, via free radical initiation, preferably photopolymerization, utilizing visible or long wavelength ultraviolet radiation and free radical, photosensitive initiators including certain dyes such as ethyl eosin, 2-methoxy-2-phenyl acetophenone, 2,2-dimethoxy-2-phenyl acetophenone, other acetophenone derivatives, camphorquinone, and the like.

Using such initiators, these polymers can be polymerized by irradiation with light at a wavelength of about 150 to about 750 nm by long wavelength or ultraviolet light, or laser light at about 514 nm.

Photooxidizable and photoreducible dyes may also be used to initiate polymerization. These include acridine dyes such as acriblarine; thiazine dyes such as thionine; xanthine dyes such as rose bengal; and phenazine dyes such as methylene blue. These can be used in conjunction with cocatalysts such as amines, sulfur compunds, imidazoles enolates, and organometallics.

Thermal polymerization initiators can also be used. These include, for example, potassium persulfate, benzoylperoxide, and ammonium persulfate with sodium bisulfite.

The polymer blends of the present invention are manufactured in the following manner. The homopolymers and copolymers are individually charged into a conventional mixing vessel having a conventional mixing device mounted therein such as an impeller. Then, the polymers and copolymers are mixed at a sufficient temperature, typically about 150° C. to about 220° C., and preferably 160° C. to 200° C., for a sufficient amount of time about 5 to about 90 minutes, more preferably for about 10 to about 45 minutes, to effectively produce a uniformly dispersed polymer blend. Then, the polymer blend is further processed in a conventional manner using conventional process equipment by removing it from the mixing device, cooling to room temperature, grinding, and drying under pressures below atmospheric at elevated temperatures for a period of time.

The polymer blends of the present invention will have sufficient amounts of poly(alkylene diglycolate)s to effectively impart a broad range of absorption profiles, and other physical properties. The blends will typically contain about 5 weight percent to about 95 weight percent, and more preferably about 10 weight percent to about 90 weight percent of poly(alkylene diglycolate) polymers.

Articles such as medical devices are molded from the polymers, copolymers and blends of the present invention by use of various conventional injection and extrusion molding processes and equipment equipped with dry nitrogen atmospheric chamber(s) at temperatures ranging from about 160° C. to about 230° C., more preferably 170° C. to about 220° C., with residence times of about 1 to about 10 minutes, more preferably about 2 to about 5 minutes.

The polymers and blends of the present invention can be melt processed by numerous methods to prepare a vast array of useful devices. These materials can be injection or compression molded to make implantable medical and surgical devices, including wound closure devices. The preferred devices are injectable defect fillers, tissue adhesives and sealants, preformed defect fillers, bone waxes, and cartilage replacements.

Alternatively, the polymers and blends can be extruded to prepare fibers. The filaments thus produced may be fabricated into sutures or ligatures, attached to surgical needles, packaged, and sterilized by known techniques. The materials of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for tying up and supporting damaged surface abrasions, particularly major abrasions, or areas where the skin and underlying tissues are damaged or surgically removed.

Additionally, the polymers and blends can be molded to form films which, when sterilized, are useful as adhesion prevention barriers. Another alternative processing technique for the polymers and blends of the present invention includes solvent casting, particularly for those applications where a drug delivery matrix is desired.

Additionally, ultrathin coatings of about 1 to about 1000 microns can be applied to tissue surfaces, including the lumen of tissue such as a blood vessel. Once applied, the coating can be cured to secure it to the tissue, making such coatings useful in the treatment or prevention of restenosis or the prevention of adhesions.

In more-detail, the surgical and medical uses of the filaments, films, foams, coatings and molded articles of the present invention include, but are not necessarily limited to knitted products, woven or non-woven, and molded products including:

a. burn dressings
b. hernia patches
c. medicated dressings
d. fascial substitutes
e. gauze, fabric, sheet, felt or sponge for liver hemostasis
f. gauze bandages g. arterial graft or substitutes
h. bandages for skin surfaces
i. burn dressings
j. orthopedic pins, clamps, screws, and plates
k. clips
l. staples
m. hooks, buttons, and snaps
n. bone substitutes
o. needles
p. intrauterine devices
q. draining or testing tubes or capillaries
r. surgical instruments
s. vascular implants or supports
t. vertebral discs
u. extracorporeal tubing for kidney and heart-lung machines
v. artificial skin and others
w. stents
x. suture anchors
y. injectable defect fillers
z. preformed defect fillers
a1. tissue adhesives and sealants
b2. bone waxes
c3. cartilage replacements
d4. tissue coatings

EXAMPLES

The following examples are illustrative of the principles and practice of this invention, although not limited thereto. Numerous additional embodiments within the scope and spirit of the invention will become apparent to those skilled in the art. The examples describe new polymers and blends of poly(alkylene diglycolate)s and aliphatic polyesters, potentially useful as biomedical devices.

In the synthetic process, the poly(alkylene diglycolate) homo- and co-polymers are prepared by a method consisting of reacting a diacid (i.e., diglycolic acid) and various multi-functional alcohols via a condensation polymerization at temperatures of 150° C. to 220° C. for 1 to 12 hours under an inert atmosphere, followed by reaction under reduced pressures for 1 to 24 hours, until the desired molecular weight and viscosity are achieved.

Furthermore, the aliphatic polyesters are prepared by a method consisting of reacting lactone monomers via a ring opening polymerization at temperatures of 80° C. to 220° C. for 1 to 24 hours under an inert nitrogen atmosphere until the desired molecular weight and viscosity are achieved.

In a another embodiment of the present invention, the copolymers of poly(alkylene diglycolate)s and aliphatic polyesters are prepared by a method consisting of reacting preformed poly(alkylene diglycolate)s with aliphatic polyesters via a transesterification at temperatures of 150° C. to 220° C. for 1 to 24 hours under an inert nitrogen atmosphere until the desired molecular weight and viscosity are achieved.

Additionally, post-polymerization reactions to form pendant acrylate groups are performed by a method consisting of reacting hydroxyl pendant side groups on poly(alkylene diglycolate) homo- and co-polymers with acryloyl chloride, or other unsaturated acid halide containing compounds such as methacryloyl chloride, transcrontonyl chloride, dimethyl acryloyl chloride, and the like, via esterification at temperatures of 25° C. to 75° C. for 1 to 12 hours under an inert atmosphere.

In the blending process, the polymer blends of the present invention are prepared by individually charging the synthesized aliphatic homo- and co-polyesters and poly(alkylene diglycolate)s into a conventional mixing vessel. The polymers and copolymers are mixed at a temperature of 150° C. to 220° C., for 5 to 90 minutes until a uniformly dispersed polymer blend is obtained.

In the examples, aliphatic polyesters and poly(alkylene diglycolate)s, and blends thereof, are prepared and based upon lactone monomers such as glycolide, lactide, p-dioxanone, trimethylene carbonate and e-caprolactone, and alkylene diglycolate monomers, including; diglycolic acid, and alcohols such as glycerol, pentaerythitol, trimethylolpropane, slightly to substantially water soluble hydroxyl terminated poly(ethylene glycol)s of weight average molecular weight of about 100 grams per mole to about 40,000 grams per mole, ethylene glycol, 1,2-propanediol, 1,3-propanediol, 1,4-butylene glycol, dipropylene glycol, 1,5-pentanediol, 1,6-hexanediol, 1,7-heptanediol, and 1,8-octanediol.

In the examples which follow, the blends, polymers and monomers were characterized for chemical composition and purity (NMR, FT-IR), thermal analysis (DSC), melt rheology (melt stability and viscosity), and molecular weight (inherent viscosity).

FT-IR was performed on a Nicolet FT-IR. Polymer samples were melt pressed into thin films. Monomers were pressed into KBr pellets. $^1$H NMR was performed on a 300 MHz NMR using $CDCl_3$ or HFAD as a reference.

Thermal analysis of blends, polymers and monomers was performed on a Dupont 912 Differential Scanning Calorimeter (DSC) at a heating rate of 10° C./min. A Fisher-Johns melting point apparatus was also utilized to determine melting points of monomers. Thermal gravimetric analysis was performed on a Dupont 951 TGA at a rate of 10° C./min. under a nitrogen atmosphere. Isothermal melt stability of the polymers was also determined by a Rheometrics Dynamic Analyzer RDA II for a period of 1 hour at temperatures ranging from 160° C. to 230° C. under a nitrogen atmosphere.

Inherent viscosities (I.V., dL/g) of the blends and polymers were measured using a 50 bore Cannon-Ubbelhode dilution viscometer immersed in a thermostatically controlled water bath at 25° C. utilizing chloroform or HFIP as the solvent at a concentration of 0.1 g/dL.

Melt viscosity was determined utilizing a Rheometrics Dynamic Analyzer RDA II at temperatures ranging from 160° C. to 230° C. at rate of 1° C./min. to 10° C./min. at frequencies of $1s^{-1}$ to $100s^{-1}$ under a nitrogen atmosphere.

Several synthesis and blend examples will be described in the following few pages. Parts and percentages where used are parts and percentages as specified as weight or moles.

EXAMPLE 1

Synthesis of a 25:75 (mol/mol) poly(1,3-propylene diglycolate -co- 2-hydroxy-1,3-propylene diglycolate) copolymer To a flame dried 250 ml 1-neck round bottom flask equipped with an overhead mechanical stirrer, vacuum adapter, 75° adapter, distillate bend with a vacuum take-off and a 50 ml collection flask, 50 grams ($3.73 \times 10^{-1}$ moles) of diglycolic acid, 14.2 grams ($1.86 \times 10^{-1}$ moles) of 1,3-propanediol, 51.5 grams ($5.59 \times 10^{-1}$ moles) of glycerol, and 8.64 microliters ($7.45 \times 10^{-6}$ moles) of a 0.33M solution of stannous octoate catalyst were added.

The assembly was then placed in a high temperature oil bath at 175° C. under a stream of nitrogen. The stirred monomers quickly began to melt. The low viscosity melt increased in viscosity. Stirring of the high viscosity melt was continued for 5 hours.

A strong vacuum was then placed on the system and a high volume of distillate (water, excess alcohol) began to evolve, and was collected. After 2 hours, the melt became very viscous. The reaction was allowed to continue for a total reaction time of 24 hours.

The 25:75 (mol/mol) rubbery, crosslinked (mol/mol) poly(propylene diglycolate -co- 2-hydroxy-1,3-propylene diglycolate) copolymer was removed from the bath, cooled to room temperature under a stream of nitrogen, and isolated. The polymer was insoluble in chloroform and hexafluroisopropanol, indicating a high degree of crosslinking or branching.

EXAMPLE 2

Synthesis of a 90:10 (mol/mol) poly(1,3-propylene diglycolate -co- 2-hydroxy-1,3-propylene diglycolate) copolymer To a flame dried 250 ml 1-neck round bottom flask equipped with an overhead mechanical stirrer, vacuum adapter, 75° adapter, distillate bend with a vacuum take-off and a 50 ml collection flask, 20 grams ($1.49 \times 10^{-1}$ moles) of diglycolic acid, 20.4 grams ($2.68 \times 10^{-1}$ moles) of 1,3-propanediol, 2.8 grams ($2.98 \times 10^{-2}$ moles) of glycerol, and 3.5 microliters ($2.98 \times 10^{-6}$ moles) of a 0.33M solution of stannous octoate catalyst were added.

The assembly was then placed in a high temperature oil bath at 175° C. under a stream of nitrogen. The stirred monomers quickly began to melt. The low viscosity melt increased in viscosity. Stirring of the high viscosity melt was continued for 5 hours.

A strong vacuum was then placed on the system and a high volume of distillate (water, excess alcohol) began to evolve, and was collected. After 2 hours, the melt became very viscous. The reaction was allowed to continue for a total reaction time of 24 hours.

The 90:10 (mol/mol) rubbery, partially crosslinked poly(propylene diglycolate -co- 2-hydroxy-1,3-propylene diglycolate) copolymer was removed from the bath, cooled to room temperature under a stream of nitrogen, and isolated. Inherent viscosity using HFIP as a solvent was 0.96 dL/g.

EXAMPLE 3

Synthesis of a 5:95 (mol/mol) poly(glycolide-co-lactide) copolymer

The method described below is similar to those described in U.S. Pat. Nos. (4,643,191, 4,653,497, 5,007,923, 5,047, 048), and should be known to those skilled in the art.

To a flame dried 500 ml 1-neck round bottom flask equipped with an overhead mechanical stirrer and nitrogen inlet, 300 grams (2.08 moles) of L(-) lactide, 12.8 grams (0.110 moles) of glycolide, 0.53 grams ($7 \times 10^{-3}$ moles) of glycolic acid initiator, and 131 microliters of a 0.33M solution of stannous octoate catalyst were added.

The assembly was then placed in a high temperature oil bath at 185° C. The stirred monomers quickly began to melt. The low viscosity melt quickly increased in viscosity. Stirring of the high viscosity melt was continued for a total reaction time of 4 hours.

The 5:95 (mol/mol) poly(glycolide-co-lactide) copolymer was removed from the bath, cooled to room temperature under a stream of nitrogen, isolated and ground. The polymer was then dried under vacuum at 110° C. for 24 hours. Inherent viscosity using HFIP as a solvent was 1.95 dL/g.

EXAMPLE 4

Synthesis of a 90:10 (mol/mol) poly(e-caprolactone-co-p-dioxanone) copolymer

The method described below is similar to those described in U.S. Pat. Nos. (4,643,191, 4,653,497, 5,007,923, 5,047, 048), and should be known to those skilled in the art.

To a flame dried 500 ml 1-neck round bottom flask equipped with an overhead mechanical stirrer and nitrogen inlet, 251.13 grams (2.2 moles) of e-caprolactone, 22.5 grams (0.22 moles) of p-dioxanone, 0.84 grams (0.011 moles) of glycolic acid initiator, and 147 microliters of a 0.33M solution of stannous octoate catalyst were added.

The assembly was then placed in a high temperature oil bath at 190° C. The stirred monomers quickly began to melt. The low viscosity melt quickly increased in viscosity. Stirring of the high viscosity melt was continued for a total reaction time of 24 hours.

The 90:10 (mol/mol) poly(e-caprolactone-co-p-dioxanone) copolymer was removed from the bath, cooled to room temperature under a stream of nitrogen, isolated and ground. The polymer was then dried under vacuum at 40° C. for 24 hours. Inherent viscosity using HFIP as a solvent was 1.17 dL/g.

EXAMPLE 5

Synthesis of a 75:25 (weight/weight) poly(e-caprolactone-co-p-dioxanone)-poly(1,3-propylene diglycolate -co- 2-hydroxy-1,3-propylene diglycolate) block copolymer composed of a 90:10 (mol/mol) poly(e-caprolactone-co-p-dioxanone) and a 90:10 (mol/mol) poly(1,3-propylene diglycolate -co- 2-hydroxy-1,3-propanediol diglycolate) copolymer 25 grams of a 90:10 (mol/mol) poly(e-caprolactone-co-p-dioxanone) copolymer prepared as described in example 4 was added along with 8.33 grams of a 90:10 (mol/mol) poly(1,3-propylene diglycolate -co- 2-hydroxy-1,3-propylene diglycolate) copolymer prepared as described in example 2, along with 2 microliters of a 0.33M solution of stannous octoate catalyst, to a flame dried 500 ml 1-neck round bottom flask equipped with an overhead mechanical stirrer and nitrogen inlet.

The assembly was then placed in a high temperature oil bath at 190° C. The stirred polymers quickly began to melt. The reaction mass was stirred for a total reaction time of 4 hours.

The 75:25 (weight/weight) blocky copolymer was removed from the bath, cooled to room temperature under a stream of nitrogen, isolated and ground. The polymer was then dried under vacuum at 40° C. for 24 hours. Inherent viscosity using HFIP as a solvent was 1.01 dL/g.

EXAMPLE 6

Synthesis of a 25:75 (weight/weight) poly(lactide-co-glycolide)-poly(1,3-propylene diglycolate -co- 2-hydroxy-1,3-propylene diglycolate) block copolymer composed of a 95:5 (mol/mol) poly(lactide-co-glycolide) and a 90:10 (mol/mol) poly(1,3-propylene diglycolate -co- 2-hydroxy-1,3-propylene diglycolate) copolymer 8.33 grams of a 95:5 (mol/mol) poly(lactide-co-glycolide) copolymer prepared as described in example 3 was added along with 25 grams of a 90:10 (mol/mol) poly(1,3- propylene diglycolate -co- 2-hydroxy-1,3-propylene diglycolate) copolymer prepared as described in example 2, along with 2 microliters of a 0.33M solution of stannous octoate catalyst, to a flame dried 500 ml 1-neck round bottom flask equipped with an overhead mechanical stirrer and nitrogen inlet.

The assembly was then placed in a high temperature oil bath at 190° C. The stirred polymers quickly began to melt. The reaction mass was stirred for a total reaction time of 4 hours.

The 25:75 (weight/weight) blocky copolymer was removed from the bath, cooled to room temperature under a stream of nitrogen, isolated and ground. The polymer was then dried under vacuum at 40° C. for 24 hours. Inherent viscosity using HFIP as a solvent was 1.36 dL/g.

EXAMPLE 7

Synthesis of a pendant acrylate terminated 90:10 (mol/mol) poly(1,3-propylene diglycolate -co- 2-hydroxy-1,3-propylene diglycolate) copolymer To a flame dried 250 ml 1-neck round bottom flask equipped with an overhead mechanical stirrer, vacuum adapter, 75° adapter, distillate bend with a vacuum take-off and a 50 ml collection flask, 20 grams of a 90:10 (mol/mol) poly(1,3-propylene diglycolate -co- 2-hydroxy-1,3-propylene diglycolate) copolymer prepared as described in example 2, and 0.52 grams (5×10–3 moles) of methacryloyl chloride in 100 ml of chloroform were added.

The assembly was then placed in an oil bath at 50° C. under a stream of nitrogen. The solution was stirred for 24 hours to allow complete evolution of hydrochloric acid.

The pendant acrylated terminated poly(alkylene diglycolate) polymer was then isolated by precipitating the chloroform solution in methanol, filtering, and drying under vacuum at 40° C. for 24 hours.

Figure 4A:
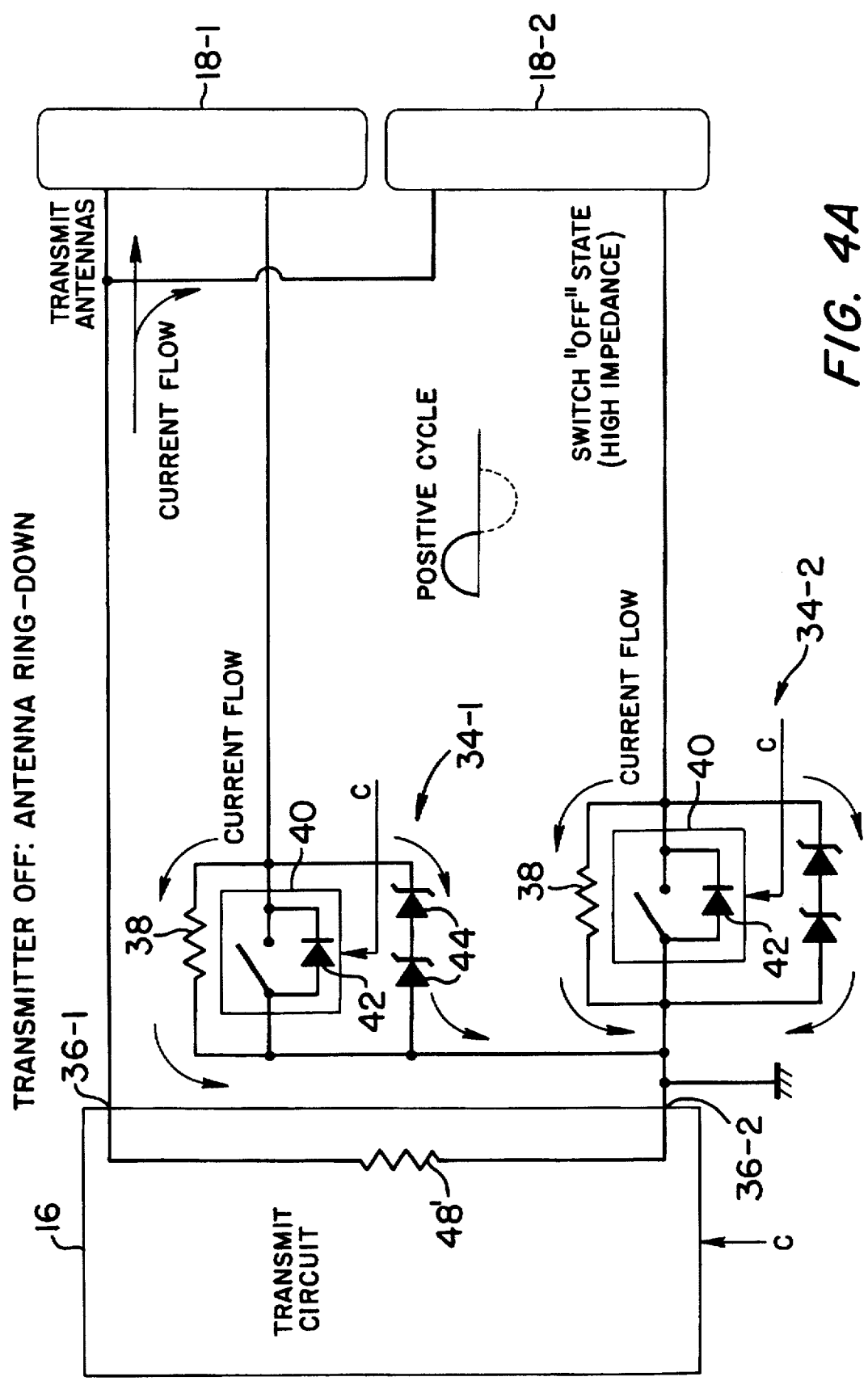
FIG. 4 illustrates the physical characteristics of branched and crosslinked poly(alkylene diglycolate) polymers as a function of reaction time and mole percent of trifunctional alcohol (i.e., glycerol) used.
Figure 4B:
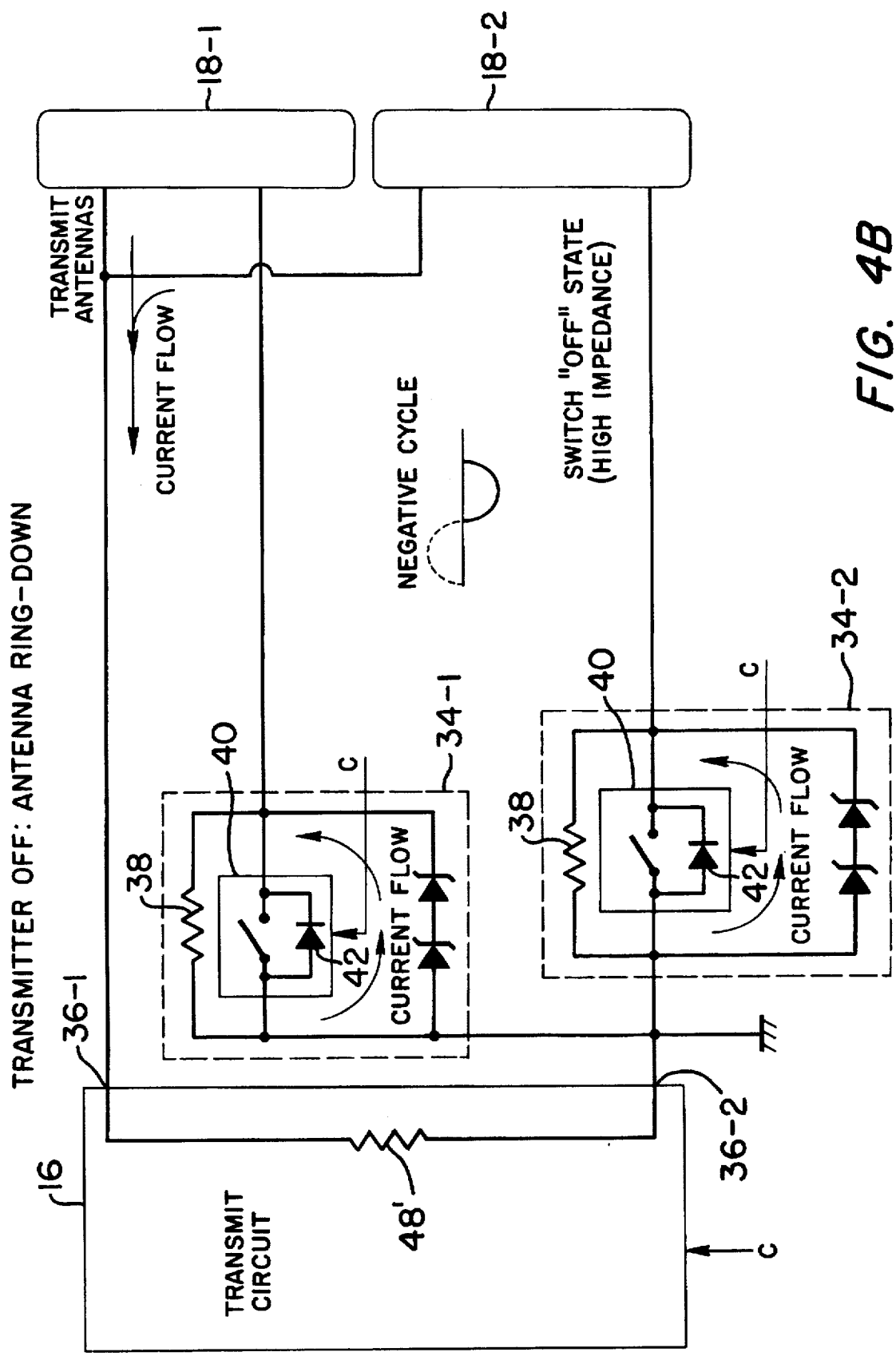
Figure 6:
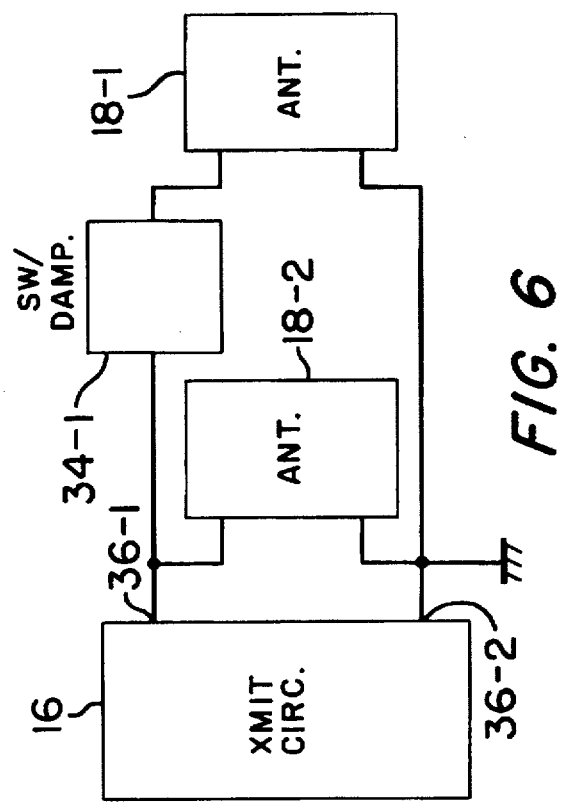
Figure 8:
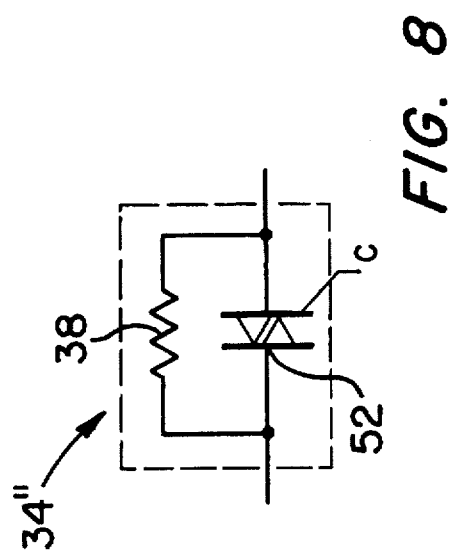
Figure 5:
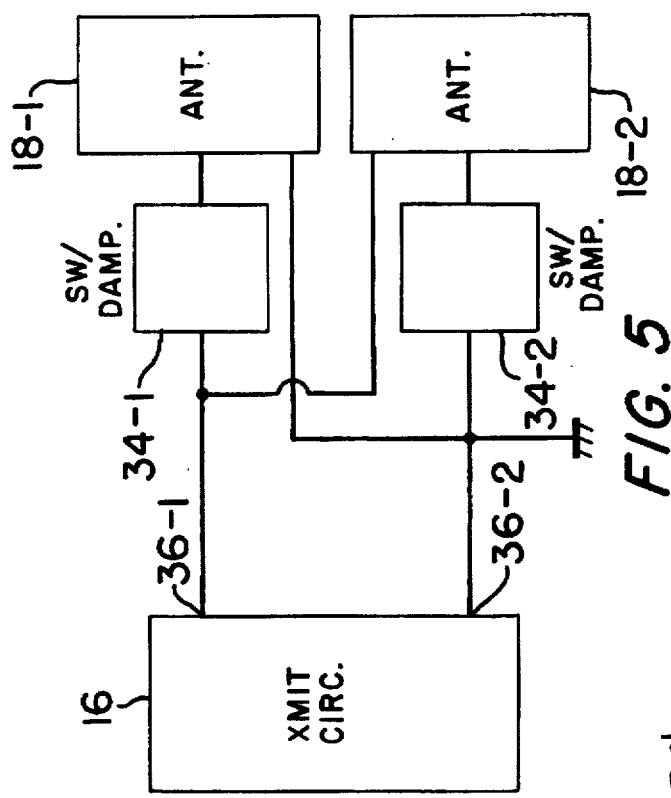
Figure 7:
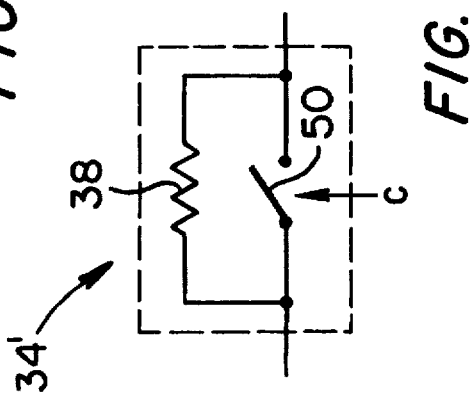

The polymers of the present invention have many advantages over the polymers of the prior art. For example as shown in FIG. 4, by incorporation of a trifunctional alcohol (i.e., glycerol) into the repeating units of a poly(alkylene diglycolate) (FIG. 1), it is possible to obtain polymers with a wide variety of physical characteristics.

That is, poly(alkylene diglycolate)s which are liquid or low melting, with only a few branch points, can be prepared by the incorporation of a small proportion of a multi-functional alcohol (i.e., glycerol) into the repeating units of the polymer chain. Additionally, highly branched or crosslinked poly(alkylene diglycolate)s can be synthesized by use of larger proportions of multi-functional alcohols.

These physical characteristics allow for a variety needs to be met for a wide range of medical devices. For example, there is a great need for polymers for use as bone waxes, and cartilage replacements. Materials for such applications should be pliable and elastic. As described above, highly branched or crosslinked, elastomeric compositions of poly (alkylene diglycolate)s, alone or in combination with other bioabsorbable aliphatic polyesters (FIG. 3), could be utilized for such applications.

Furthermore, biomedical applications such as defect fillers, and tissue adhesives and sealants require characteristics such as hydrophilicity, ease of application (i.e., low viscosity liquid) and quick setting times (i.e., water or light curing). As described above, liquid or low melting, slightly branched poly(alkylene diglycolate)s could be utilized for such applications when post-reacted to form pendant acrylate groups which can be cured by UV light (FIG. 2) to form tough, crosslinked, elastic films.

Although useful for drug delivery applications, linear, low Tg, poly(alkylene diglycolate)s do not have the characteristics of elasticity or toughness, due to a lack of crosslinks or branching, required for biomedical devices such as preformed implants (i.e., cartilage replacements).

Furthermore, linear poly(alkylene diglycolate)s do not have pendant functional groups (i.e., alcohol substitutients) which can be post-polymerized to form crosslinks. This, as described above, is useful for applications, such as tissue adhesives, which require ease of application (i.e., low viscosity), but solidification (i.e., in-situ crosslinking) after being applied.

Therefore, the branched or crosslinked poly(alkylene diglycolate)s of the present invention yield a broad range of properties such as elasticity and toughness, which can not be found with linear poly(alkylene diglycolate)s. This allows the branched or crosslinked polymers of the present invention to be utilized in a variety of medical devices where linear poly(alkylene diglycolate)s can not be used.

Although this invention has been shown and described with respect to detailed embodiments thereof, it will understood by those skilled in the art that various changes in form and detail thereof may be made without departing from the spirit and scope of the claimed invention.

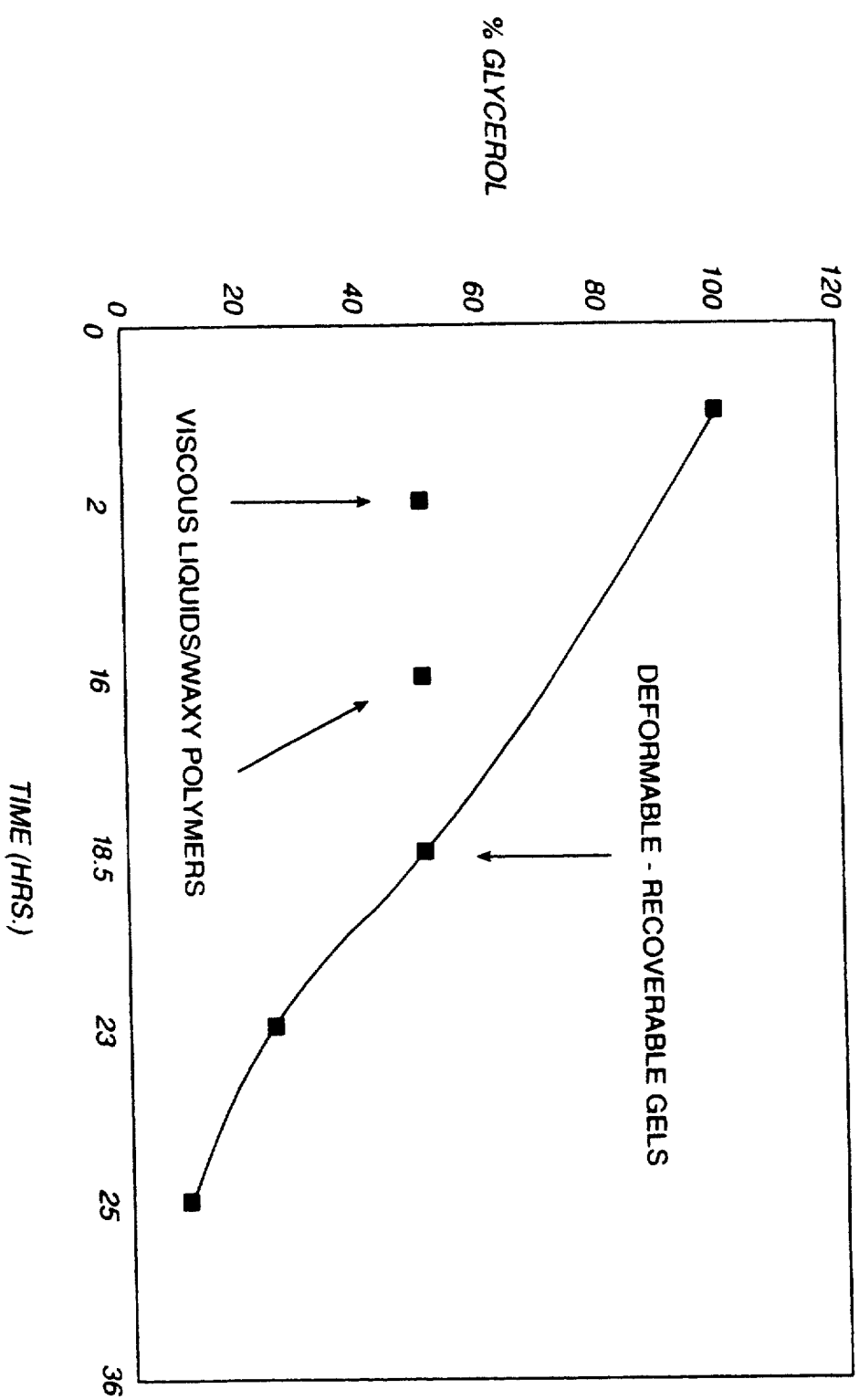

We claim:

1. An absorbable, biocompatible poly(alkylene diglycolate) comprising the reaction product of:
    an acid or ester of diglycolic acid; and,
    an alcohol selected from the group consisting of glycerol, pentaerythitol, trimethylolpropane, hydroxyl terminated poly(ethylene glycol)s, ethylene glycol, 1,2-propanediol, 1,3-propanediol, 1,4-butylene glycol, dipropylene glycol, 1,5-pentanediol, 1,6-hexanediol, 1,7-heptanediol, and 1,8-octanediol,
    wherein the poly(alkylene diglycolate) comprises about 10 mole percent to about 90 mole percent of repeating units with tri-, tetra-alcohols, and hydroxyl terminated poly(ethylene glycol)s, and wherein the balance of the poly(alkylene diglycolate) comprises repeating units with diol alcohols and
    wherein the poly(alkylene diglycolate) polymer additionally comprises pendant acrylate groups.

2. The pendant acrylate terminated polymer of claim 1 wherein the polymer is cured via free radical photopolymerization, utilizing irradiation selected from the group consisting of visible and long wavelength ultraviolet radiation at a wavelength of about 150 to about 750 nm and laser light at about 514 nm, and free radical, photosensitive initiators selected from the group consisting of ethyl eosin, 2-methoxy-2-phenyl acetophenone, 2,2-dimethoxy-2-phenyl acetophenone, and camphorquinone.

* * * * *

UNITED STATES PATENT AND TRADEMARK OFFICE
CERTIFICATE OF CORRECTION

PATENT NO. : 5,736,589
DATED : April 7, 1998
INVENTOR(S) : Kevin Cooper, et. al.

It is certified that error appears in the above-identified patent and that said Letters Patent is hereby corrected as shown below:

The Drawings should be deleted and replaced with the attached drawings

Signed and Sealed this

Seventeenth Day of November, 1998

Attest:

BRUCE LEHMAN

Attesting Officer

Commissioner of Patents and Trademarks

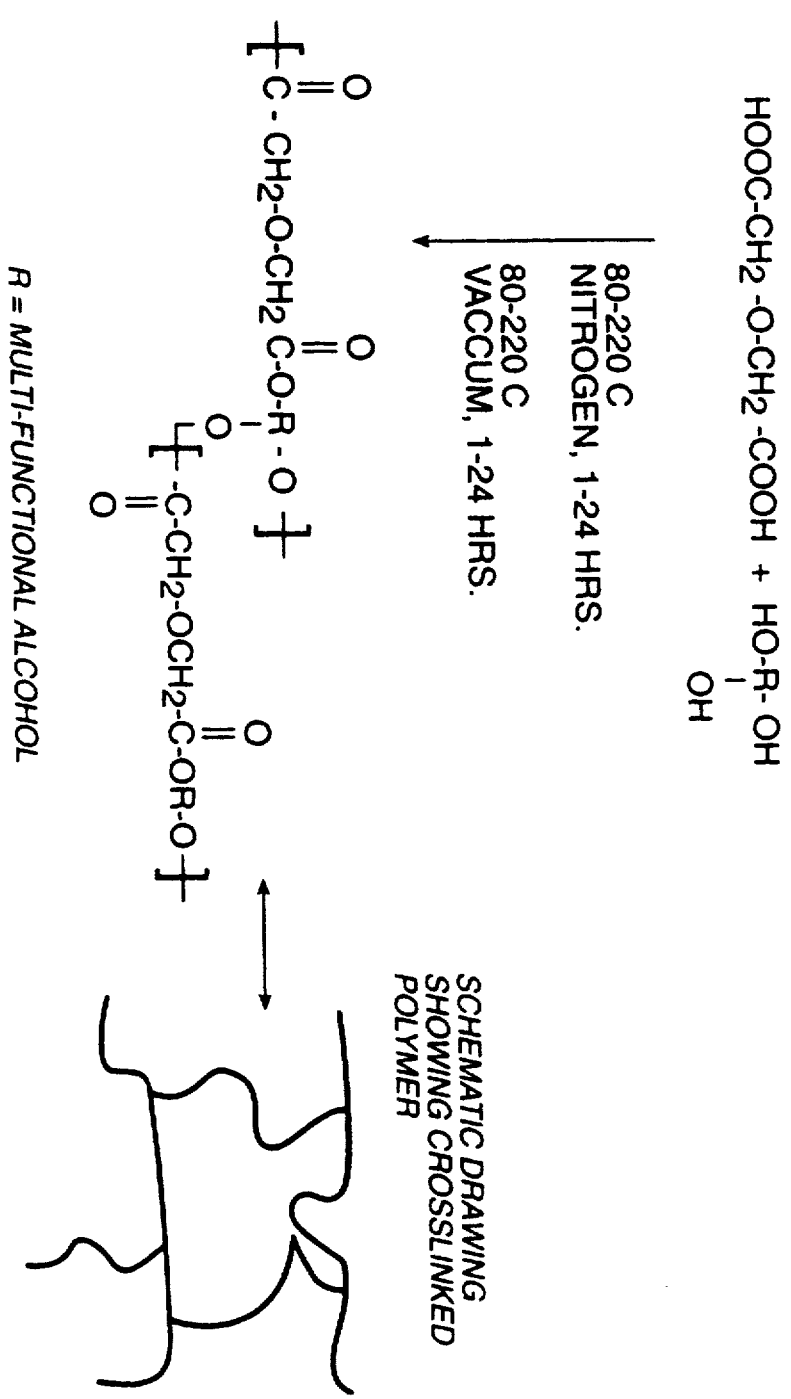
FIG. 1 SYNTHESIS OF BRANCHED AND CROSSLINKED POLY(ALKYLENE DIGLYCOLATE)S

FIG. 2 SYNTHESIS OF PHOTOCURABLE POLY(ALKYLENE DIGLYCOLATE) POLYMERS
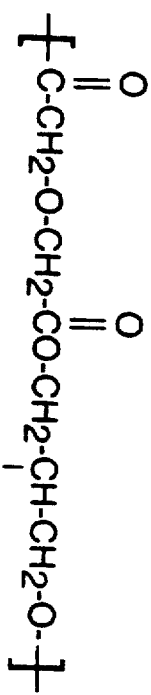
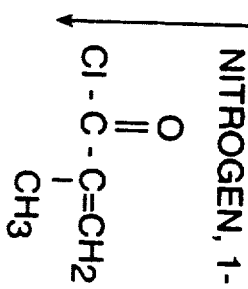
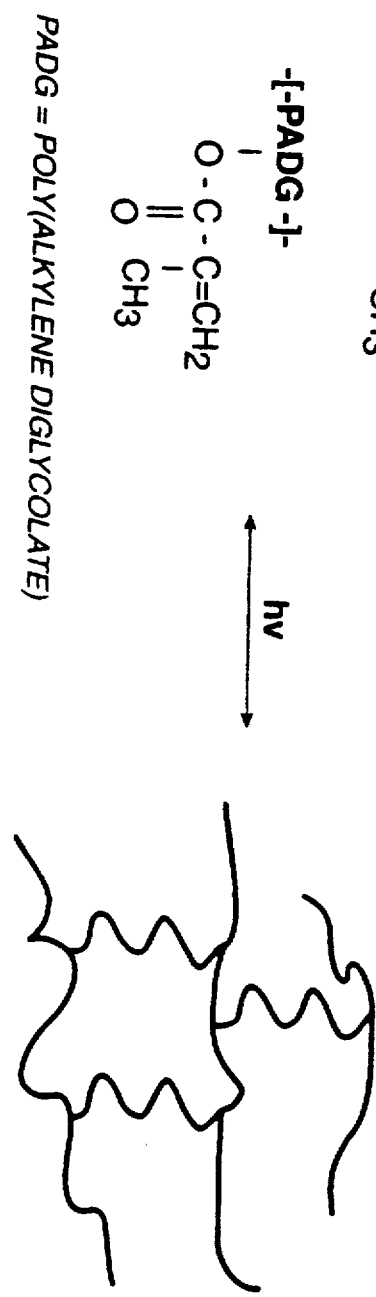
SCHEMATIC DRAWING SHOWING CROSSLINKED POLYMER AFTER PHOTOCURING
PADG = POLY(ALKYLENE DIGLYCOLATE)

Figure 3B:
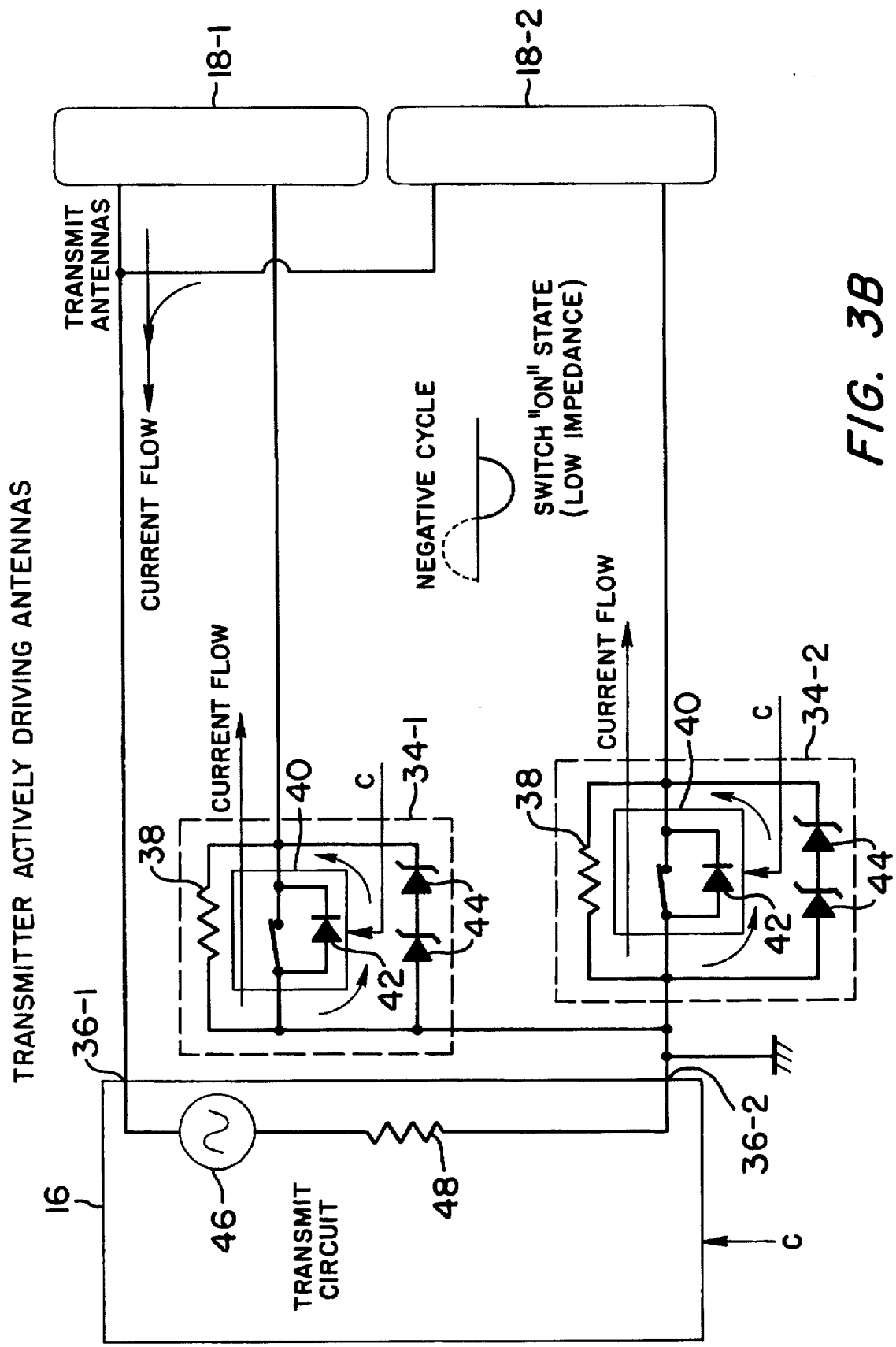

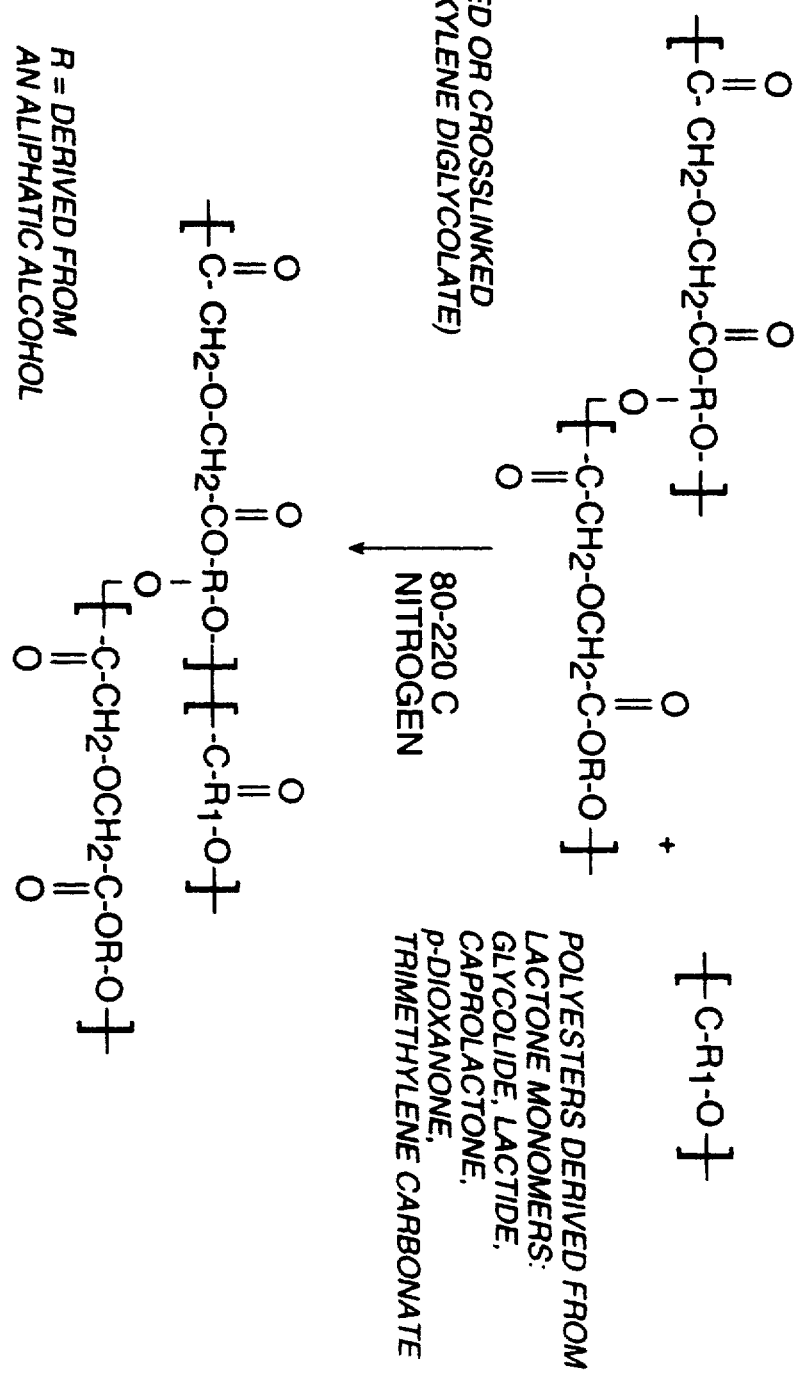
FIG. 3 SYNTHESIS OF POLY(ALKYLENE DIGLYCOLATE-CO-LACTONE ESTER) COPOLYMERS